United States Patent [19]

Merchat et al.

[11] Patent Number: 5,361,989

[45] Date of Patent: Nov. 8, 1994

[54] DEVICE FOR GENERATING A MIST FROM A LIQUID, ESPECIALLY A MEDICATION

[75] Inventors: Serge Merchat; Jose Teixeira, both of Grenoble; Gérard Cinquin, Villeneuve-sur-Lot, all of France

[73] Assignee: D.P. Medical, Meylan, France

[21] Appl. No.: 134,733

[22] Filed: Oct. 12, 1993

[51] Int. Cl.⁵ .............................................. B05B 17/06
[52] U.S. Cl. ................... 239/102.2; 239/524
[58] Field of Search ............... 239/102.1, 102.2, 524, 239/512, 338

[56] References Cited

U.S. PATENT DOCUMENTS

| | | | |
|---|---|---|---|
| 3,387,607 | 6/1968 | Gauthier et al. | 239/102.2 |
| 3,690,317 | 9/1972 | Millman | 239/102.1 |
| 3,828,773 | 8/1974 | Buch et al. | 239/102.2 |
| 3,838,686 | 10/1974 | Szekely | 239/338 |
| 5,170,782 | 12/1992 | Kocinski | 239/338 |
| 5,235,969 | 8/1993 | Bellm | 239/338 |

FOREIGN PATENT DOCUMENTS

| | | | |
|---|---|---|---|
| 3225951 | 1/1984 | Germany | 239/102.2 |
| 3826101 | 2/1990 | Germany | |
| 82209 | 6/1980 | Japan | 239/102.2 |
| 262321 | 1/1970 | U.S.S.R. | 239/102.2 |

OTHER PUBLICATIONS

Patent Abstracts of Japan, vol. 009, No. 104 (C-279) 8 Mar. 1985 & JP-A-59 230 658 (Koushin KK) 25 Dec. 1984 (Abstract).
Patent Abstracts of Japan, vol. 4, No. 186 (C-36) 20 Dec. 1980 & JP-A-55 124 566 (Tokyo Shibaura Denki KK) 25 Dec. 1980.

*Primary Examiner*—Karen B. Merritt
*Attorney, Agent, or Firm*—Armstrong, Westerman, Hattori, McLeland & Naughton

[57] ABSTRACT

A device for generating a mist from a liquid by a vibrating device. The device comprises a chamber which has a bottom wall on which the liquid rests, a side wall and a top wall. The chamber has at least one mist outlet orifice. The device includes a deflector which has a preferably concave or inclined underside at a distance above the bottom of the chamber and at a level lower than that of the top wall of the chamber.

15 Claims, 8 Drawing Sheets

DEVICE FOR GENERATING A MIST FROM A LIQUID, ESPECIALLY A MEDICATION

BACKGROUND OF THE INVENTION

1. Field of the Invention

The present invention concerns an improvement to devices for generating a mist from a liquid, a medication to be inhaled, for example.

2. Description of he Prior Art

The device includes a chamber with a bottom wall on which a pool of the liquid rests, a side wall and a top wall. The mist is generated in said chamber by means of a vibrating member, the chamber having at least one exit orifice for the mist.

SUMMARY OF THE INVENTION

The invention consists in a device for generating a mist from a liquid by means of a vibrating member and comprising a chamber which has a bottom wall on which the liquid rests, a side wall and a top wall which incorporates at least one mist outlet orifice, in which device said vibrating member is a distance below said bottom wall of said chamber, said side wall of said chamber has a narrower lower part, the upper side of said bottom wall surrounded by said narrower wall is concave and a deflector in the lower part of said chamber is disposed at a level below that of said top wall of said chamber and has an underside at a distance above the bottom of said chamber, at least part of the edge of said deflector being at a small distance from said narrower lower part of said side wall of said chamber.

When the mist is formed in said chamber an upward jet of droplets is produced at the surface of the liquid. The deflector of the invention constitutes an obstacle which reduces or prevents splashing of the liquid droplets against the side or top wall of said chamber, where they could otherwise remain due to capillary action with the result that they would not be converted into mist.

As the vibrating member usually operates on the bottom part of the chamber where the pool of liquid lies, the deflector of the invention can considerably increase the quantity of liquid which is converted into mist from a dose of liquid introduced into said chamber.

The deflector of the invention can convert into mist a dose of liquid whose volume is very much less than the volume of said chamber. The underside of the deflector advantageously has at least one concave or inclined part.

The underside of said deflector advantageously has at least one flat part.

This flat part is preferably inclined.

The deflector preferably comprises a plate one side of which constitutes said underside.

The upper side of the deflector is preferably convex.

The deflector advantageously has a downwardly projecting part on the underside.

The deflector is preferably carried by at least one wall of the chamber.

In one embodiment of the invention the deflector is suspended from the upper wall of the chamber.

In another embodiment of the invention the deflector bears against the bottom and/or the side wall of the chamber.

The deflector and at least one wall of the chamber may have mutually interengaging parts.

In one embodiment of the invention the deflector is carried by at least one wall of the chamber by means of at least one arm.

The deflector is preferably removably installed in the chamber.

The device advantageously comprises a cup with a concave bottom which constitutes the bottom and side walls of the chamber and a lid which constitutes its top wall.

The present invention will be better understood from the following description of a device for generating a mist from a liquid equipped with deflectors given by way of non-limiting example only and with reference to the accompanying drawings.

DETAILED DESCRIPTION OF THE INVENTION

Figure 1:
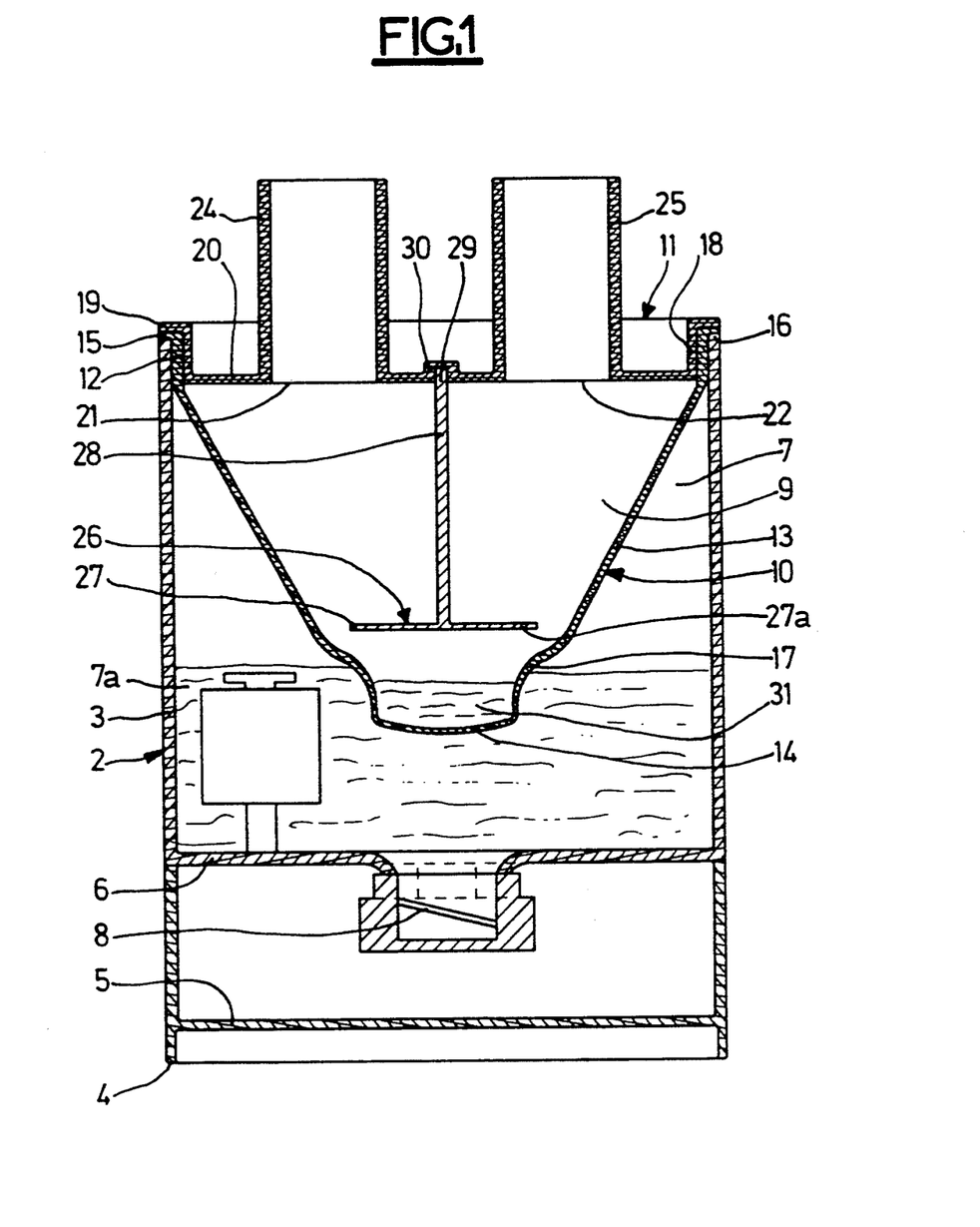
FIG. 1 is a vertical cross-section of a device for generating a mist from a liquid contained in a chamber equipped with a first embodiment of a deflector.
Figure 2:
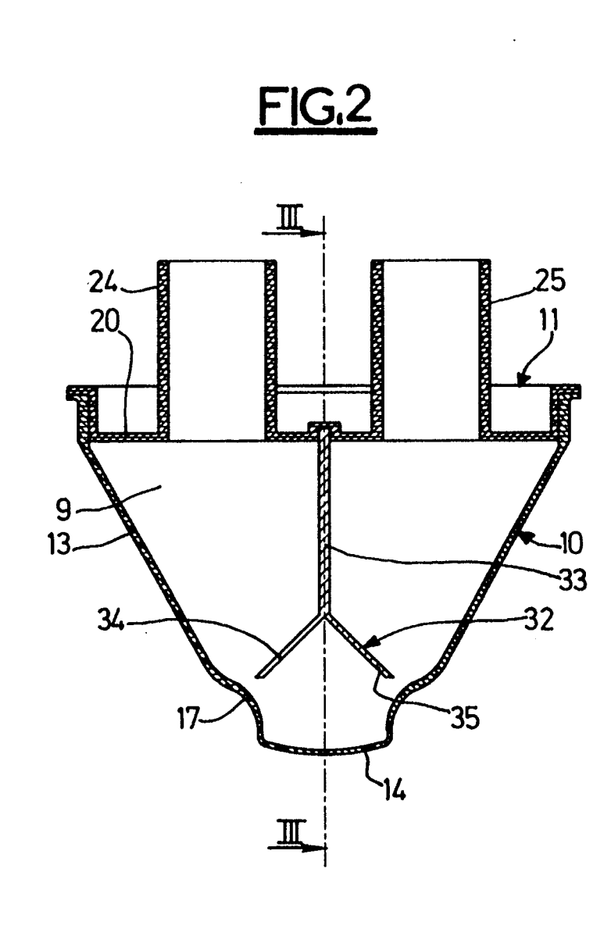
FIG. 2 is a median vertical cross-section through the chamber of the device equipped with a second embodiment of a deflector.
Figure 3:
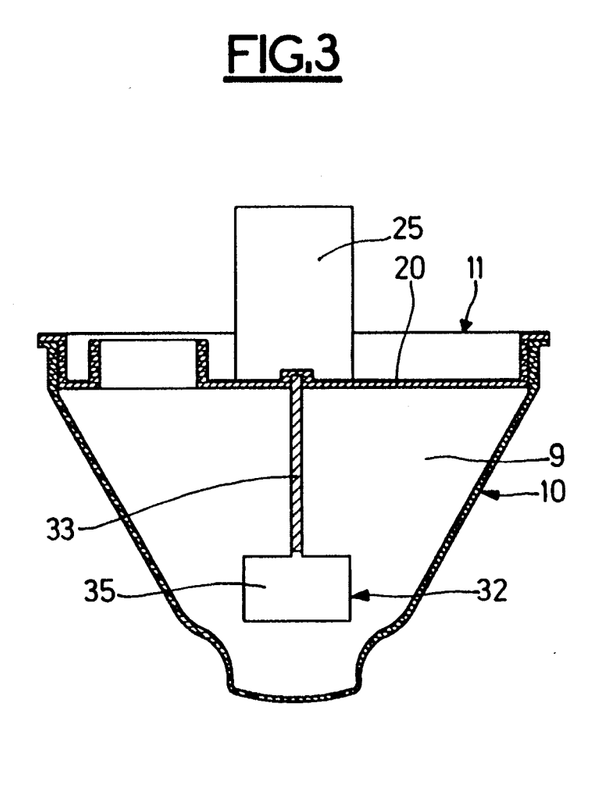
FIG. 3 is a median vertical cross-section through the chamber on the line III—III in FIG. 2.
Figure 4:
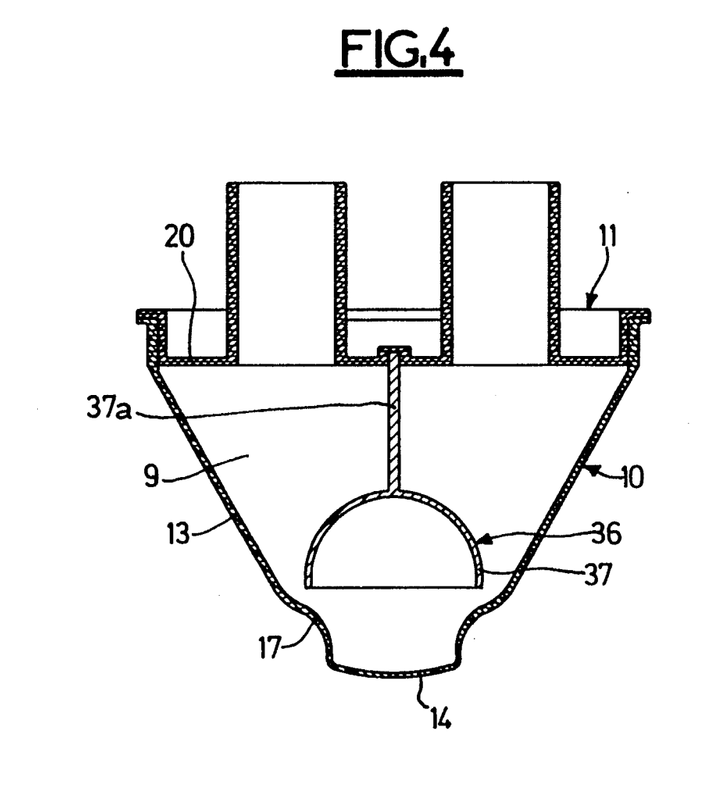
FIG. 4 is a median vertical cross-section through the chamber of the device equipped with a third embodiment of a deflector.

FIG. 1 shows a device for generating a mist from a liquid.

The device comprises a support 2 which has a cylindrical peripheral wall 3 whose axis is vertical and whose lower edge 4 is adapted to rest on a horizontal supporting surface. The support further comprises, inside the cylinder 3, a lower horizontal radial wall 5 and an intermediate horizontal radial wall 6 above which is an open-topped space 7.

The intermediate wall 6 carries at its center a vibrating member 8 in the form of a quartz crystal (for example), the support 2 carrying means (not shown) for activating this member adapted to be connected to a source of electrical energy.

The device comprises a chamber 9 delimited by a cup 10 disposed inside the space 7 of the support 2 and a lid 11.

In the direction from the top towards the bottom the cup 10 has a short cylindrical part 12, a frustoconical part 13 of reducing diameter and a bottom wall 14 spaced from the intermediate radial wall 6 of the support 2. The cylindrical part 12 is inserted with a small clearance in the upper part of the peripheral wall 3 of the support 2 and has a rim 15 which rests on the upper edge 16 of the wall 3. The bottom wall 14 of the cup 10 has a concave upper side and the lower part 17 of the frustoconical part 13 has a slightly smaller diameter than the remainder.

The lid 11 comprises a short cylindrical part 18 which fits with a small clearance into the cylindrical part 12 of the cup 10 and has an exterior annular rim 19 which bears on the rim 15 of the cup and a horizontal disk 20 with two openings 21 and 22 from which extend tubes 24 and 25 for connecting external pipes (not shown).

The lid 11 stacks in the cup 10 and this combination is removable for placing the liquid in the cup 10.

In the chamber 9 is a deflector 26 comprising a parallel-sided horizontal disk 27 and a vertical suspension member 28 extending upwardly therefrom. The disk 27 and the member 28 are coaxial with the cup 10. The upper end 29 of the member 28 is engaged in an opening 30 in the disk 20 of the lid, i.e. the deflector 26 is suspended from the lid.

The length of the member 28 is such that the underside 27a of the disk 27 of the deflector 26 is substantially one quarter of the way along the distance between the bottom wall 14 of the cup 10 and the underside of the disk 20 of the lid 11.

The diameter of the disk 27 of the deflector 26 is slightly larger than the diameter of the bottom wall 14 of the cup 10 and is at a small distance from the narrower part 17 of the frustoconical side wall 13 of the cup 10 so that a gap remains between its edge and the latter.

A dose of liquid 31 rests in the bottom of the cup 10 with its upper surface at a distance below the underside 27a of the disk 27 of the deflector 26. The volume of the dose 31 (a few cubic millimeters) is very much less than the volume of the chamber 9.

A liquid 7a such as water partially fills the space 7 up to a level such that the lower part of the cup 10 is immersed to transmit vibrations from the quartz crystal 8 to the liquid 31.

When the quartz crystal 8 is activated a mist comprising very fine droplets of liquid is generated at the surface of the liquid 31. This mist passes between the edge of the disk 27 of the deflector 26 and the frustoconical side wall 13 of the cup 10 and is drawn off by a flow of air across the chamber 9 from one tube 24 or 25 to the other produced by external means (not shown).

The quartz crystal 8 generates an upward jet localized at the surface of the liquid 31. This jet impinges on the underside 27*a* of the disk 27 of the deflector 26 with the result that there is virtually no splashing of liquid droplets above the level of the disk 27 towards the frustoconical wall 13 or towards the disk 20 of the lid 11. Also, liquid droplets splashed onto the disk of the deflector 26 drop off again.

Due to the effect of the deflector and more specifically the combined effects of the deflector 26 and the concave end wall 14 of the cup 10 it is possible to convert virtually all of the dose 31 of liquid poured into the cup 10 into mist without any liquid droplets remaining on the side wall 13 of the cup 10 or on the wall 20 of the lid 11.

If the deflector 26 is not to be used, for example if much larger quantities of liquid are to be converted into mist, all that is required is to remove the lid 11, separate the deflector 26 from it by disengaging the end 29 of the member 28 from the hole 30 and replace the lid 11 on the cup 10 as previously.

Various other embodiments of the deflector will now be described with reference to the other figures.

In the FIGS. 2 and 3 embodiment the deflector 32 is removably suspended from the lid 11 as previously, by means of a vertical arm 33. Instead of the disk 27 it comprises two inclined rectangular plates 34 and 35 which are symmetrical and joined together at their upper edge, from which the arm 33 extends. The lower edges of the plates 32 and 34 are at a small distance from the narrower part 17 of the side wall 13 of the cup 10.

This arrangement has the advantage that it forces the droplets or the jet of liquid striking the lower side of the plates 34 and 35 to drop off again. Moreover, if liquid droplets are deposited onto the upper surfaces of the plates 34 and 35 they drop off again rather than collecting there.

In the embodiment shown in FIG. 4 the deflector 36 comprises a wall 37 in the shape of a dome or an inverted wineglass suspended from the lid 11 by an arm 37*a* as in the previous example. The lower edge of the dome 36 is at a small distance from the narrower part 17 of the wall 13 of the cup 10. This deflector has a concave lower side facilitating recycling of splashed droplets and a convex upper side so that any droplets which might be deposited on its upper side drop off.

The FIG. 5 embodiment varies from the FIG. 4 embodiment only in that the deflector 36 has at the center of the lower surface of the wall 37 a pointed part 38 projecting downwards. The projecting part 38 also facilitates downward movement of any droplets which form on the underside of the deflector.

The deflector 39 shown in FIGS. 6 and 7 differs from the deflector shown in FIG. 4 only in that it is not symmetrical. It has a shorter side 40 and a longer side 41 which extends to within a small distance of the narrower part 17 of the cup 10.

In the example shown in FIGS. 8 and 9 the deflector 42 is no longer suspended from the lid 11 by an arm. It comprises a plate folded to a V-shape with the upper ends of its branches 43 and 44 bearing elastically against pegs 45 and 46 on the lower side of the disk 20 of the lid 11. The width of the plate 42 is substantially equal to the diameter of the lower end wall 14 of the cup 10. Its branches 43 and 44 are parallel to the frustoconical side wall of the cup 10 and its rounded point 47 is at a small distance from and faces the bottom wall 14 of the cup 10. The edges of the lower part 47 of the deflector 42 are a small distance from the narrower part 17 of the cup 10.

The deflector 48 in the FIG. 10 embodiment differs from that in FIGS. 8 and 9 only in that the plate constituting it has a depressed apex 49 so that it has a concave lower surface facing the bottom wall 14 of the cup 10.

In the remaining embodiments the deflector is no longer suspended from the lid 11 of the chamber but is supported by the wall of the cup 10, for example by resting on at least one inwardly deformed part of the side wall or the bottom wall of the cup or a part provided specifically for this purpose.

Figure 11:
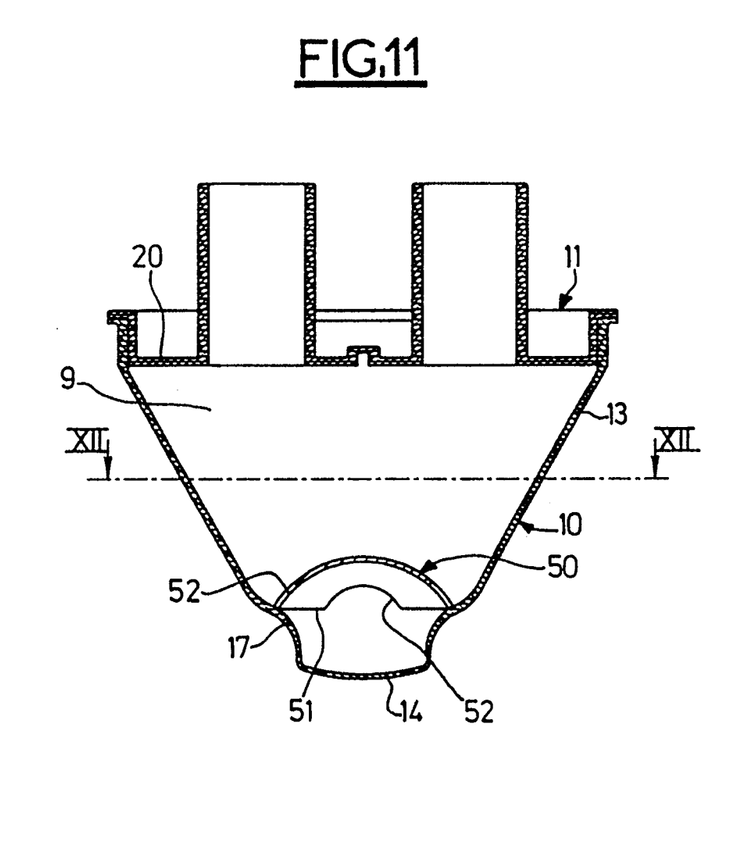
FIG. 11 is a median vertical cross-section through the chamber of the device equipped with a sixth embodiment of a deflector.
Figure 12:
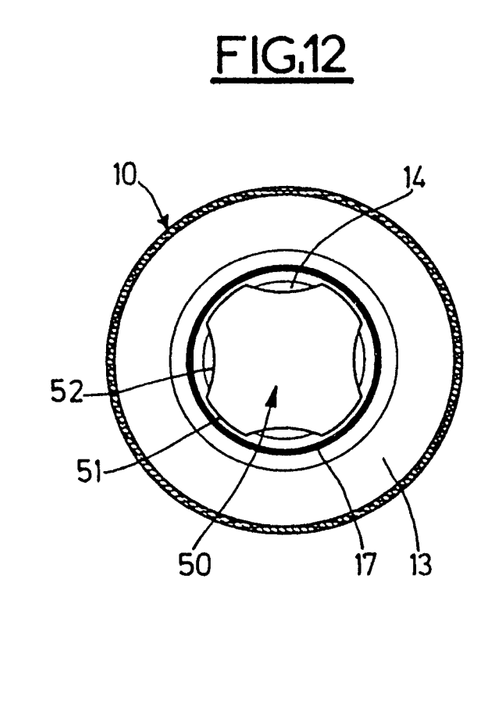
FIG. 12 is a horizontal cross-section through the chamber on the line XII—XII in FIG. 11.

In the embodiment of FIGS. 11 and 12 the deflector 50 is formed by a domed plate whose axis is on the vertical axis of the cup 10. Its edge 51 comprises four notches 52 between which it rests on the upper edge of the narrower part 17 of the side wall 13 of the cup 10. The edge of the notches 52 is a small distance from the narrower part 17 of the cup 10.

As in the previous examples the jet or droplets of splashed liquid impinge on the concave lower side of the deflector 50, any droplets which may form on its convex upper side dropping off via the notches 52 and the mist formed being evacuated through the notches 52.

Figure 5:
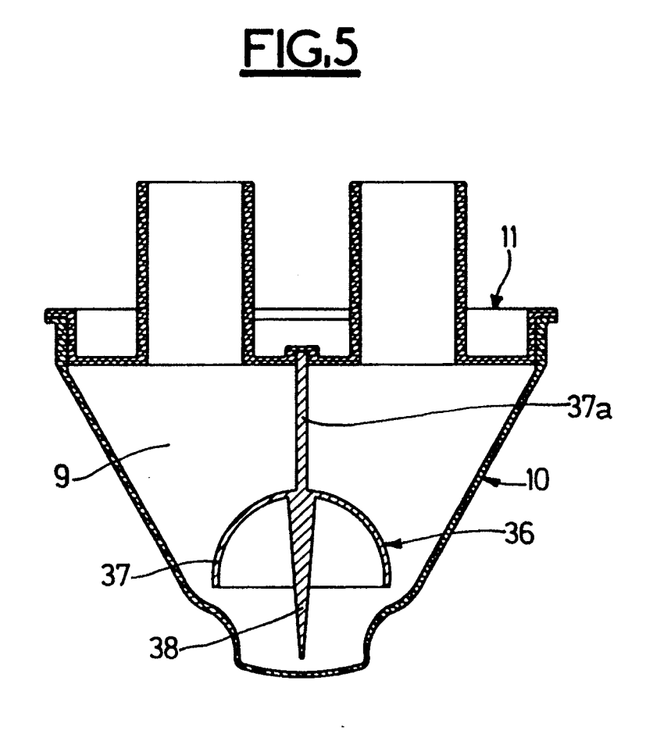
FIG. 5 is a median vertical cross-section through a variant of the FIG. 4 deflector.
Figure 6:
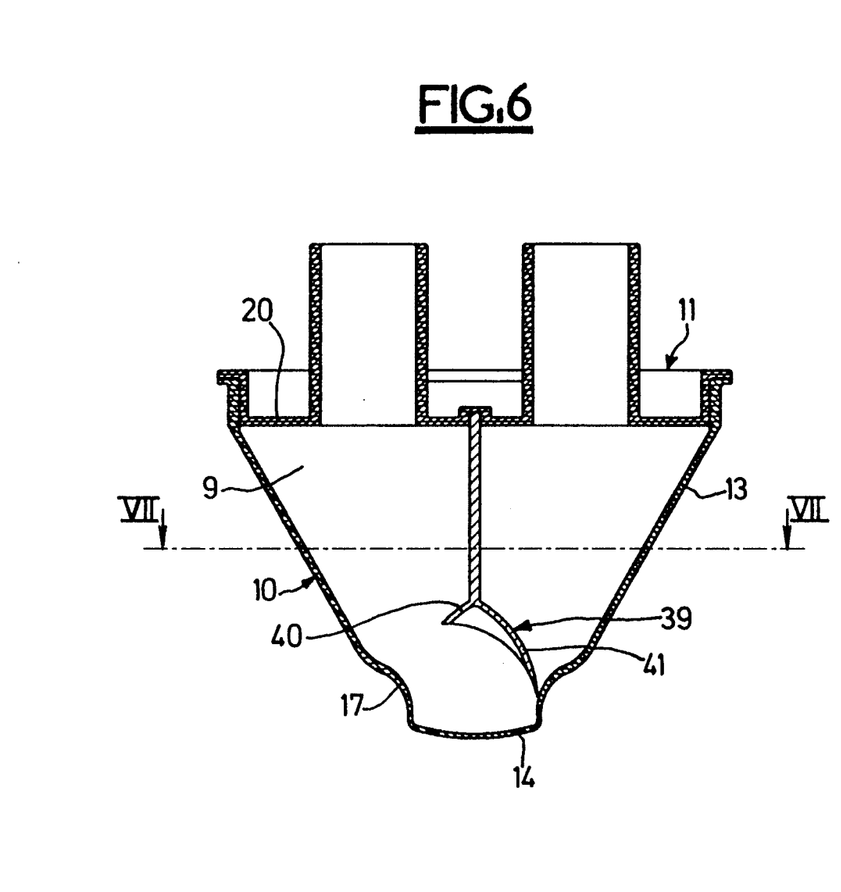
FIG. 6 is a median vertical cross-section through the chamber of the device equipped with a fourth embodiment of a deflector.
Figure 7:
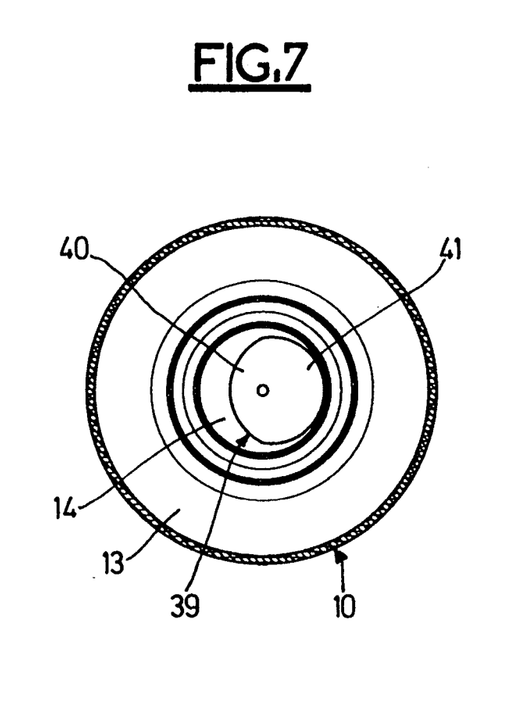
FIG. 7 is a horizontal cross-section through the chamber on the line VII—VII in FIG. 6.
Figure 8:
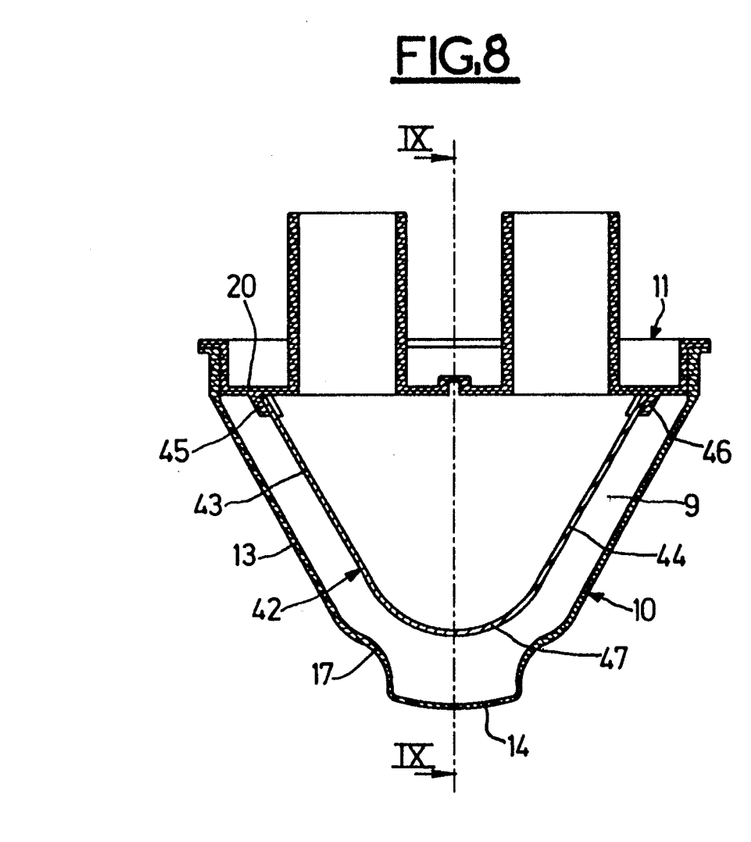
FIG. 8 is a median cross-section through the chamber of the device equipped with a fourth embodiment of a deflector.
Figure 9:
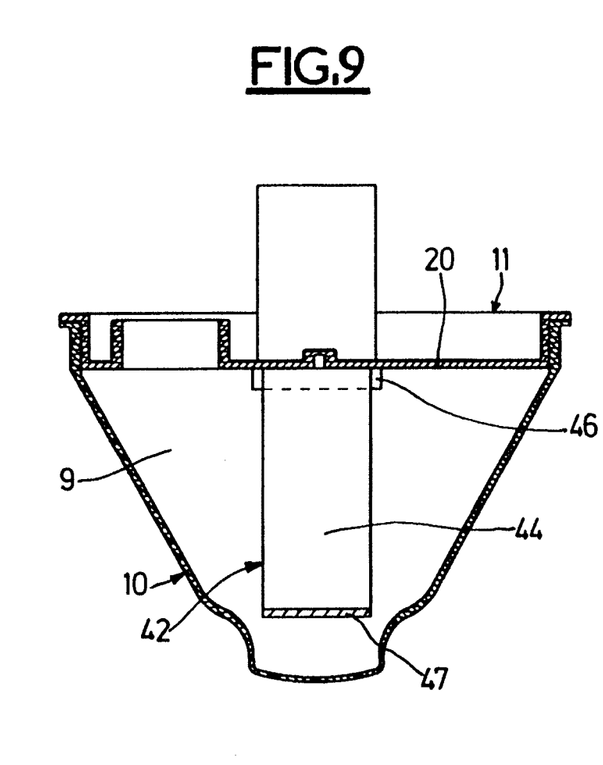
FIG. 9 is a median vertical cross-section through the chamber on the line IX—IX in FIG. 8.
Figure 10:
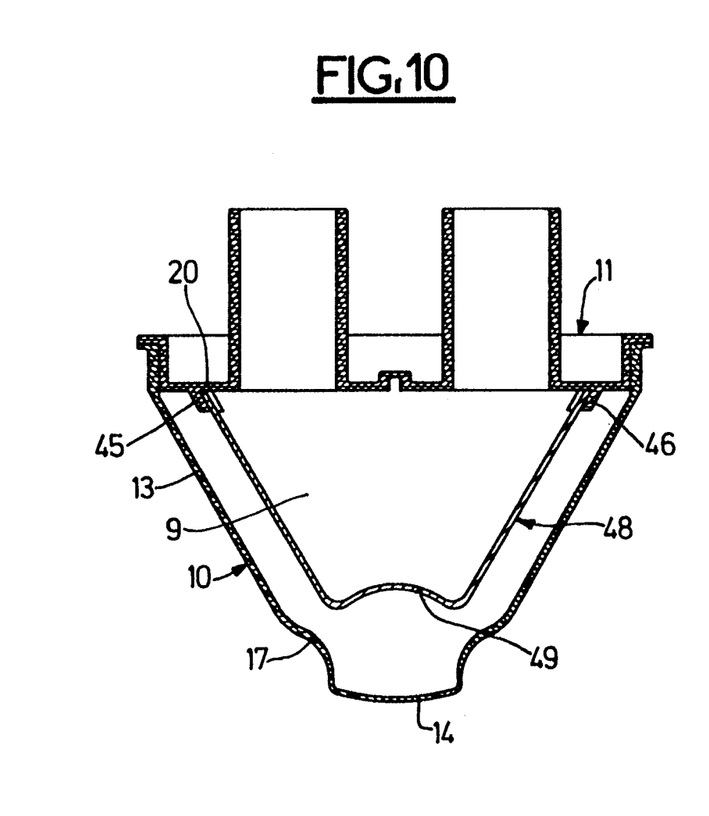
FIG. 10 is a median vertical cross-section through the chamber of the device equipped with a fifth embodiment of a deflector.
Figure 13:
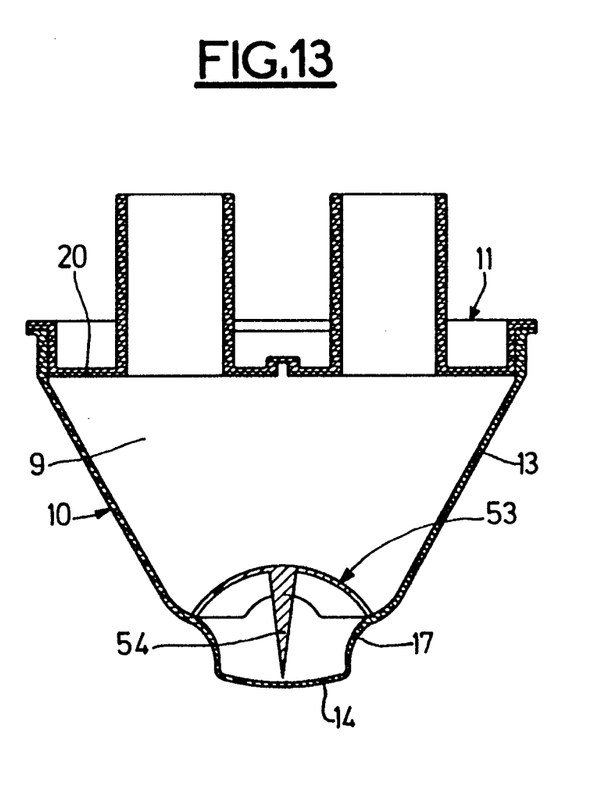
FIG. 13 is a median vertical cross-section through a variant of the FIG. 5 deflector.

The deflector 53 in FIG. 13 differs from the deflector 50 only in that its lower side has a pointed part 54 projecting axially towards the bottom wall 14 of the cup 10. The function of this projecting part is the same as in FIG. 5.

Figure 14:
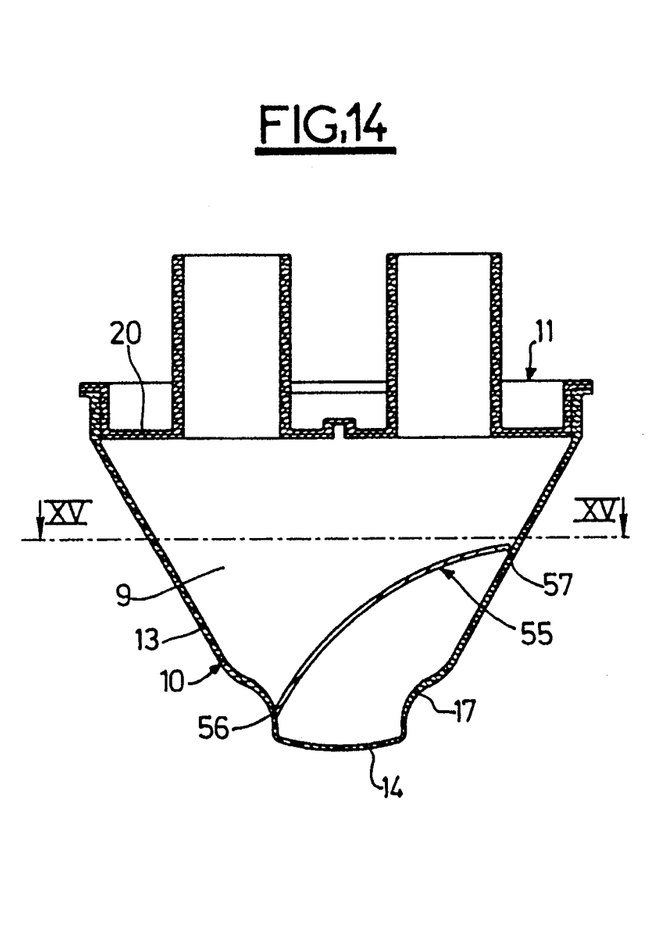
FIG. 14 is a median vertical cross-section through the chamber of the device equipped with a seventh embodiment of a deflector.
Figure 15:
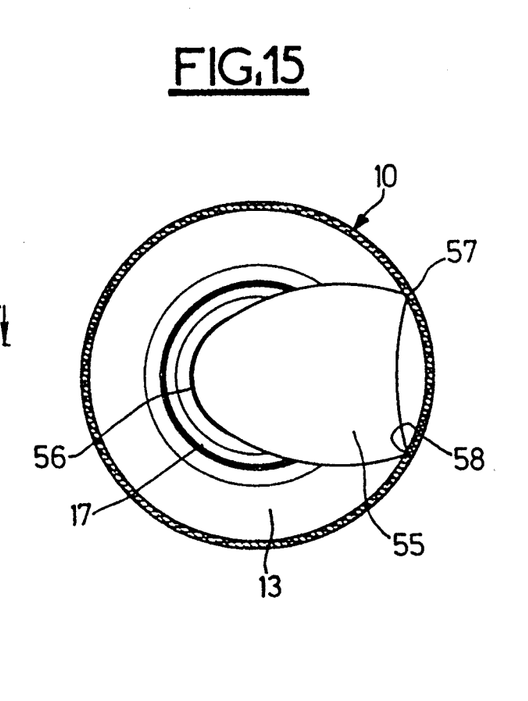
FIG. 15 is a horizontal cross-section through the chamber on the line XV—XV in FIG. 11.

In the embodiment of FIGS. 14 and 15 the deflector 55 is formed by a substantially triangular plate with the lower corner 56 rounded and resting on a part of the upper edge of the narrower part 17 of the side wall 13 of the cup 10. Its other two corners 57 and 58 bear against the side wall 13 of the cup 10, approximately half way up it and on the opposite side of the cup axis. The underside of the deflector 55 is concave and its upper side is convex for the same reasons as previously. The mist formed can flow upwards between the sides of the deflector 55 and the frustoconical wall 13 of the cup 10. The sides of the deflector 55 and the frustoconical wall 13 of the cup 10 are a small distance apart, in particular near the narrower part 17 of the cup.

The present invention is not limited to the examples described above. Many variants thereof can be envisaged without departing from the scope of the appended claims.

There is claimed:

1. Device for generating a mist from a liquid comprising
   a chamber for receiving the liquid and having a bottom wall, a side wall and a top wall provided with at least one mist outlet orifice,
   a vibrating member which is located a distance below said bottom wall of said chamber and emits a vibration towards the bottom wall of said chamber for generating a jet at a surface of the liquid,
   said side wall of said chamber having a narrower lower part surrounding said bottom wall
   a deflector disposed in said chamber at a distance from said at least one mist outlet orifice,
   means for connecting said deflector to said top wall of the chamber, said deflector being at a level or distance below said top wall of said chamber and having an underside at a distance above and covering substantially the bottom wall of said chamber,
   at least part of a edge of said deflector being at a small distance from said narrower lower part of said side wall of said chamber,
   whereby the jet formed at the surface of the liquid impinges on an underside of said deflector so that there is virtually no splashing of liquid droplets above the level of said deflector towards said top wall, said at least one mist outlet orifice or the part of said side wall located above said narrower lower part thereof and that the mist formed passes between the edge of said deflector and said side wall towards an upper space of said chamber situated over said deflector before being evacuated through said at least one mist outlet orifice, therefore small quantities of liquid can be virtually completely converted into mist.

2. Device according to claim 1 wherein said underside of said deflector has at least one concave part.

3. Device according to claim 1 wherein said underside of said deflector has at least one flat part.

4. Device according to claim 3 wherein said at least one flat part is inclined.

5. Device according to claim 1 wherein said deflector comprises a plate, one side of which forms said underside.

6. Device according to claim 1 wherein an upper side of said deflector is convex.

7. Device according to claim 1 wherein said deflector has a part projecting downwardly from said underside.

8. Device according to claim 1 wherein said deflector rests on said side wall of said chamber.

9. Device according to claim 1 wherein said means for connecting comprises said deflector and said top wall of said chamber having mutually interengaging parts.

10. Device according to claim 1 wherein said deflector is carried by said top wall of said chamber by means of at least one arm.

11. Device according to claim 1 wherein said deflector is removably installed in said chamber.

12. Device according to claim 1 wherein a cup having a concave bottom constitutes said bottom and side walls of said chamber and a lid constitutes said top wall, said cup being disposed in a tank having a bottom carrying said vibrating member.

13. Device according to claim 1 wherein an upper side of deflector is inclined.

14. Device according to claim 1, wherein said top wall is a removable lid and wherein said deflector is provided with at least one arm extending upwardly, an upper part of said arm and said lid having mutually interengaging parts for suspending said deflector from said lid and removably installing said deflector in said chamber.

15. Device according to claim 14, wherein said deflector comprises a wall in the shape of a dome suspended from said lid by said arm, the lower edge of said dome being at a small distance from said narrower part of the side wall of said chamber.

* * * * *